(12) United States Patent
Hamilton

(10) Patent No.: US 7,339,058 B2
(45) Date of Patent: Mar. 4, 2008

(54) PROCESS FOR THE PREPARATION OF N-([1,2,4]TRIAZOLOPYRIMIDIN-2-YL)ARYL SULFONAMIDES

(75) Inventor: Christopher Thomas Hamilton, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 296 days.

(21) Appl. No.: 11/088,448

(22) Filed: Mar. 24, 2005

(65) Prior Publication Data

US 2005/0215570 A1   Sep. 29, 2005

Related U.S. Application Data

(60) Provisional application No. 60/557,022, filed on Mar. 26, 2004.

(51) Int. Cl.
*C07D 487/04* (2006.01)
*A61K 31/519* (2006.01)

(52) U.S. Cl. ..................... 544/263; 544/254
(58) Field of Classification Search ........... 544/263; 514/259.31
See application file for complete search history.

(56) References Cited

U.S. PATENT DOCUMENTS

| | | | | |
|---|---|---|---|---|
| 5,177,206 | A | 1/1993 | Johnson et al. | 544/263 |
| 5,858,924 | A * | 1/1999 | Johnson et al. | 504/241 |
| 5,973,148 | A * | 10/1999 | Ringer et al. | 544/263 |
| 6,518,222 | B2 | 2/2003 | Arndt et al. | 504/241 |
| 6,559,101 | B2 | 5/2003 | Johnson et al. | 504/241 |

* cited by examiner

*Primary Examiner*—Brenda L. Coleman
*Assistant Examiner*—Susanna Moore
(74) *Attorney, Agent, or Firm*—Craig E. Mixan

(57) ABSTRACT

The N-arylsulfilimine-catalyzed coupling of aromatic sulfonyl chlorides with N-([1,2,4]triazolopyrimidin-2-yl)amines to form N-([1,2,4]triazolo-pyrimidin-2-yl)aryl sulfonamides is improved by the selection of 3-picoline or 3,5-lutidine as the base.

3 Claims, No Drawings

PROCESS FOR THE PREPARATION OF N-([1,2,4]TRIAZOLOPYRIMIDIN-2-YL)ARYL SULFONAMIDES

CROSS REFERENCES TO RELATED APPLICATIONS

This application claims the benefit of U.S. Provisional Application No. 60/557,022 filed Mar. 26, 2004.

BACKGROUND OF THE INVENTION

The present invention relates to the use of N-([1,2,4]-triazolopyrimidin-2-yl)sulfilimine compounds as catalysts in the reaction of aromatic sulfonyl chloride compounds with N-([1,2,4]triazolopyrimidin-2-yl)amines to form N-([1,2,4]triazolopyrimidin-2-yl)aryl sulfonamide compounds.

More particularly, the present invention concerns an improved process in which 3-picoline or 3,5-lutidine is used as the base in the sulfilimine catalyzed coupling.

Recently, a series of N-([1,2,4]triazolopyrimidin-2-yl)aryl sulfonamides have been found to be valuable herbicides; see, for example, U.S. Pat. Nos. 5,858,924; 6,518,222; and 6,559,101. The preparation of triazolopyrimidine sulfonamides in general and N-([1,2,4]triazolopyrimidin-2-yl)aryl sulfonamides in particular by the reaction of aromatic sulfonyl chloride compounds with N-([1,2,4]triazolopyrimidin-2-yl)amine compounds typically gives unsatisfactory results because the reaction is slow and the yields are poor and susceptible to impurities in the raw materials. U.S. Pat. No. 5,177,206 teaches that a mixture of a pyridine base and dimethyl sulfoxide gave improved coupling results in many instances. U.S. Pat. No. 5,973,148 teaches that sulfilimines in the presence of an aromatic tertiary amine base also facilitate this coupling in certain cases. Nevertheless, the preparation of N-([1,2,4]triazolopyrimidin-2-yl)aryl sulfonamides wherein the aromatic sulfonyl chloride compound possesses one or, especially, two ortho-substituents is often particularly unsatisfactory because of the steric deactivation effect and, when the substituents are electron-rich, the electronic deactivation effect of ortho-substituents. Even though aromatic nitrogen heterocycles have long been known to catalyze the reaction of many sulfonyl chloride compounds with amines to form sulfonamides, methods of obtaining N-([1,2,4]triazolopyrimidin-2-yl)aryl sulfonamides more readily and in improved yields are desirable.

SUMMARY OF THE INVENTION

It has now been found that the use of 3-picoline or 3,5-lutidine as the base greatly improves the sulfilimine-catalyzed reaction of aromatic sulfonyl chlorides with N-([1,2,4]triazolopyrimidin-2-yl)amines to form N-([1,2,4]-triazolopyrimidin-2-yl)aryl sulfonamides. The effect is especially significant in such reactions involving a relatively unreactive aromatic sulfonyl chloride compound and/or a relatively unreactive aromatic amine compound. Faster rates of reaction, reduced sulfilimine amounts, and improved yields are obtained.

The invention concerns an improved process for the preparation of an N-([1,2,4]triazolopyrimidin-2-yl)-aryl sulfonamide of formula I:

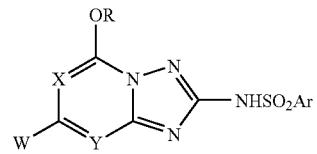

wherein
  X represents CH or N;
  Y represents CZ or N with the proviso that one of X or Y is N;
  W represents H or OR with the proviso that when Y represents CZ, then W represents H;
  Z represents OR;
  R represents $CH_3$ or $CH_2CH_3$;
Ar represents

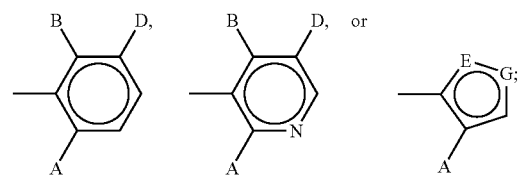

wherein
  A and B independently represent H, halo, $CF_3$, R or $OR^1$;
  D represents H, halo or R;
  E and G represent S or CB with the proviso that one of E or G is S; and
  $R^1$ represents $C_1$-$C_4$ alkyl, $C_3$-$C_4$ alkenyl, or $C_3$-$C_4$ alkynyl each optionally possessing up to two chloro, bromo or $C_1$-$C_4$ alkyl substituents or up to the maximum possible number of fluoro substituents which comprises combining a sulfonyl chloride compound of the formula:

wherein
  Ar is defined as above with an amine compound of the formula:

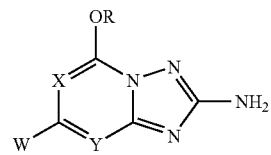

wherein
  R, X, Y and W are defined as above in the presence of an aromatic tertiary amine base, an inert solvent, and a catalytic amount of an N-arylsulfilimine compound of the formula:

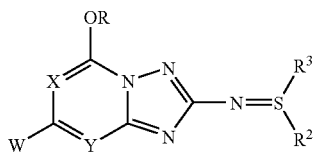

wherein
R, X, Y and W are defined as above;
$R^2$ represents $CH_3$, or $CH_2CH_3$; and
$R^3$ represents $R^2$ or $R^2$ and $R^3$ together represent tetramethylene in which the improvement comprises using 3-picoline or 3,5-lutidine as the aromatic tertiary amine base.

It is greatly preferred that the N-([1,2,4]triazolopyrimidin-2-yl) group in the sulfilimine compound be selected to be identical with the N-([1,2,4]-triazolopyrimidin-2-yl) amine compound.

The selection of 3-picoline or 3,5-lutidine as the base provides higher yields when stoichiometric ratios of amine and sulfonyl chloride are used, provides faster reaction times, allows lower temperature conversion, requires less sulfilimine catalyst, and improves economy with respect to equivalents of base. An important result of these attributes is that the reaction can be performed in good yield under a wider range of conditions including qualities of feeds, presence of inerts, and choices of solvents.

DETAILED DESCRIPTION OF THE INVENTION

The catalytic N-arylsulfilimine compounds used in the invention, which can be represented by the formula A:

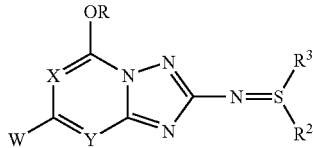

or, alternatively, by the formula B:

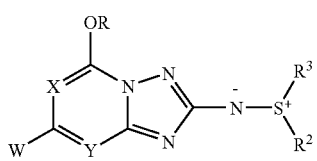

are characterized by having a semipolar nitrogen-sulfur bond. This bond can be depicted as a double bond, the sulfur atom of which is tetravalent as in formula A, or can be depicted as single bond, the nitrogen atom of which is negatively charged and the sulfur atom of which is positively charged as in formula B. Compounds possessing such bonds are often referred to as ylides. It should be understood that these compounds may be portrayed in various resonance forms in which, for example, the negative charge can reside on other nitrogen atoms of the triazolopyrimidine system. For simplicity, the sulfilimine compounds of the invention are depicted herein as being compounds having the structure of formula A with the understanding that these compounds are the same as compounds depicted as having the structure of formula B or resonance forms thereof. The sulfilimine compounds can also be prepared, isolated, and employed as their salts with acids such as HCl and HBr.

The substituents on the sulfur atom are $R^2$ and $R^3$ wherein $R^2$ represents methyl or ethyl, and $R^3$ represents $R^2$, or wherein $R^2$ and $R^3$ together represent tetramethylene. Such compounds wherein $R^2$ and $R^3$ both represent methyl are generally preferred.

The terms alkyl, alkenyl, and alkynyl (including when modified as in haloalkyl and alkoxy) as used herein include straight chain, branched chain, and cyclic groups. Thus, typical alkyl groups are methyl, ethyl, 1-methylethyl, propyl, 1,1-dimethylethyl, and cyclopropyl. Methyl and ethyl are often preferred. Alkyl groups are sometimes referred to herein as normal (n), iso (i), secondary (s) or tertiary (t). Typical alkyl with up to the maximum possible number of fluoro substituents include trifluoromethyl, monofluoromethyl, 2,2,2-trifluoroethyl, 2,2-difluoroethyl, and the like; trifluoromethyl and 2,2-difluoroethyl is often preferred. The term halogen includes fluorine, chlorine, bromine, and iodine.

The N-arylsulfilimine compounds of formula A can be prepared by several general methods known in the art. The methods described in *Chemical Reviews*, 77, 409-435 (1977), *Synthesis*, 165-185 (1981), *Journal of Organic Chemistry*, 552-555 (1982), and *Russian Chemical Reviews*, 59, 819-831 (1990) and the references cited therein can be used with only routine adaptation.

One method of preparation involves the reaction of a sulfoxide compound of the formula:

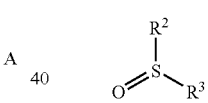

wherein $R^2$ and $R^3$ are as previously defined, with an N-([1,2,4]triazolopyrimidin-2-yl)amine compound of formula:

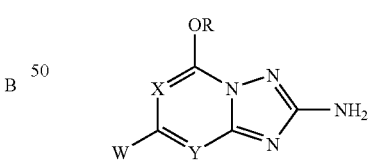

wherein R, X, Y and W are as previously defined and an activator such as sulfur trioxide, 2-sulfobenzoic acid cyclic anhydride, trifluoroacetic anhydride, phosgene, oxalyl chloride or an aliphatic or aromatic sulfonyl chloride. The reaction mixture is treated with a base, such as an tertiary aromatic amine, to complete the process. The process is generally carried out at temperatures between about −70° C. and about 20° C. in an organic solvent, such as dichloromethane. For example, a mixture of the N-([1,2,4]triazolopyrimidin-2-yl)amine compound, sulfoxide compound and tertiary aromatic amine are combined in the reaction solvent, cooled to the desired reaction temperature, and the activator compound is then added. The mixture is then stirred for 1-12 hours, sometimes accompanied by an adjustment in the temperature, to complete the reaction. The N-arylsulfilimine compound product can often be recovered in its salt form by direct filtration from the reaction mixture, or can be isolated and purified by conventional means. It is not always necessary to recover the sulfilimine product from the reaction mixture, and is often advantageous to combine the mixture, in a catalytic quantity, with the N-([1,2,4]triazolopyrimidin-2-yl)amine compound, aromatic sulfonyl chloride, and additional 3-picoline or 3,5-lutidine to produce the desired sulfonamide product.

Alternately, the N-arylsulfilimine compounds of Formula A can be prepared by the reaction of a sulfide compound of the formula $R^2$—S—$R^3$ with an N-([1,2,4]triazolopyrimidin-2-yl)amine compound and chlorine or bromine. The process is generally carried out at temperatures between about −30° C. and about 20° C. in an organic solvent, such as dichloromethane or acetonitrile. Typically, a solution of the sulfide compound in the solvent is prepared and cooled to the desired reaction temperature. Approximately one molar equivalent of chlorine or bromine is added. After a short reaction period, the N-([1,2,4]triazolopyrimidin-2-yl)amine compound is added, and the mixture stirred for 1-12 hours at a specified temperature range which may be higher than the initial temperature. The specified temperature range varies with the amine substrate, but is usually within the range of about −30° C. and about 20° C. The N-arylsulfilimine product is formed as a slurry of its hydrochloride or hydrobromide salt in the organic solvent, and can be recovered by filtration or can be used by direct combination of the sulfilimine reaction mixture with the coupling reaction mixture, as described for the previous method.

An alternate method of preparation involves using a chlorinating or brominating agent such as N-chlorosuccinimide or N-bromosuccinimide in place of chlorine or bromine. Thus, the N-([1,2,4]triazolopyrimidin-2-yl)amine compound and alkyl sulfide are combined in an organic solvent such as methylene chloride and acetonitrile and cooled to the desired reaction temperature, usually between about −30° C. and about 20° C. The chlorinating agent is added, typically as a solution in an organic solvent such as methylene chloride or acetonitrile, at a rate to keep the temperature within a desired range which varies by amine substrate. The N-arylsulfilimine is formed as its hydrochloride or hydrobromide salt that can typically be isolated by filtration of the reaction mixture.

In all of the methods described, the N-arylsulfilimine product typically contains some amount (1-50%) of the unreacted starting amine. This does not effect the performance of the compound, although the composition needs to be considered when selecting the amount of material to employ.

The N-arylsulfilimine compounds of Formula A are useful as catalysts or activators in the preparation of N-([1,2,4] triazolopyrimidin-2-yl)aryl sulfonamides of formula I:

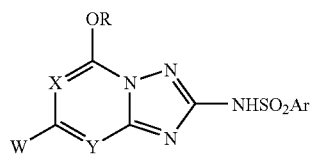

I wherein
X represents CH or N;
Y represents CZ or N with the proviso that one of X or Y is N;
W represents H or OR with the proviso that when Y represents CZ, then W represents H;
Z represents OR;
R represents $CH_3$ or $CH_2CH_3$;
Ar represents

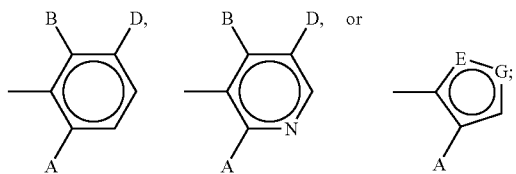

wherein
A and B independently represent H, halo, $CF_3$, R or $OR^1$;
D represents H, halo or R;
E and G represent S or CB with the proviso that one of E or G is S; and
$R^1$ represents $C_1$-$C_4$ alkyl, $C_3$-$C_4$ alkenyl, or $C_3$-$C_4$ alkynyl each optionally possessing up to two chloro, bromo or $C_1$-$C_4$ alkyl substituents or up to the maximum possible number of fluoro substituents by the reaction of aromatic sulfonyl chloride compounds of formula:

$ArSO_2Cl$ wherein
Ar is defined as above
with an N-([1,2,4]triazolopyrimidin-2-yl)amine of formula:

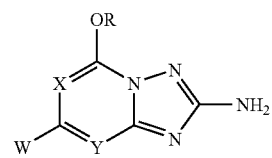

wherein
R, X, Y and W are defined as above.

The improved process is carried out by contacting an aromatic sulfonyl chloride compound with an N-([1,2,4] triazolopyrimidin-2-yl)amine in the presence of 3-picoline or 3,5-lutidine and an added catalytic amount of an N-arylsulfilimine compound of Formula A (or salt thereof):

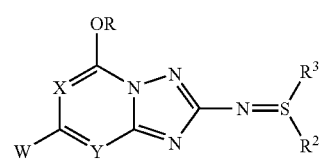

A wherein R, X, Y, W, $R^2$ and $R^3$ are as defined hereinabove.
Any of the known procedures for contacting the reactants and catalyst can be used. For example, the sulfonyl chloride compound, a molar equivalent of a N-([1,2,4]triazolopyrimidin-2-yl)amine, 4-6 molar equivalents or more of 3-picoline or 1-4 molar equivalents or more of 3,5-lutidine, and a catalytically effective amount (1-10 molar percent) of an N-arylsulfilimine (or salt thereof) are combined in an organic solvent. It is sometimes preferred to have a slight excess of sulfonyl chloride, although stoichiometrically equal amounts are typically used to maximize the efficiency of both reagents. The reagents can be combined in any order. It is frequently preferred to prepare the N-arylsulfilimine catalyst in a vessel and add the N-([1,2,4]triazolopyrimidin-2-yl)-amine, the aromatic sulfonyl chloride, the 3-picoline or 3,5-lutidine, and additional reaction solvent to it. The N-([1,2,4]triazolopyrimidin-2-yl)amine can be present during the preparation of the N-arylsulfilimine catalyst; that is, an excess of N-([1,2,4]triazolopyrimidin-2-yl)amine can be used in the preparation of the N-arylsulfilimine catalyst and the excess employed as all or a portion of the N-([1,2,4]triazolopyrimidin-2-yl)amine reactant in the process. The desired N-([1,2,4]triazolopyrimidin-2-yl)aryl sulfonamide is prepared in the resulting reaction. It is often most preferred to form the N-arylsulfilimine in situ by reacting the aromatic sulfonyl chloride, the N-([1,2,4]triazolopyrimidin-2-yl) amine and a sulfoxide, most preferably dimethyl sulfoxide, in the presence of 3-picoline or 3,5-lutidine and an inert solvent.

A catalytically effective amount of the N-arylsulfilimine compounds of formula A can be determined readily for each N-(1,2,4]triazolopyrimidin-2-yl)aryl sulfonamide preparation by routine experimentation. In most instances, an amount between about 1 and about 10 mole percent of the amount of aromatic sulfonyl chloride compound is employed, more preferably between about 1 and about 6 mole percent of the amount of aromatic sulfonyl chloride.

The process is generally carried out at a temperature of between about –20° C. and about 65° C. The lower limit is because the reaction becomes too slow to be practical at very low temperatures and the higher limit is because the N-arylsulfilimine catalysts become unstable and degradation/side reactions increase at elevated temperatures. Temperatures of between about room temperature and about 50° C. are often preferred. The pressure in the reactor is not believed to be critical; pressures close to atmospheric are generally preferred. Continuous and effective mixing is usually helpful. A reaction period of 2 hours to about 24 hours is typical for the process to go to completion. The reaction is generally carried out under essentially anhydrous conditions.

Solvents that are suitable for such processes are organic solvents in which the aromatic sulfonyl chloride compound, the N-arylsulfilimine compound, and the arylamine compound have at least some solubility and which are inert with respect to the reagents employed. Suitable solvents include acetonitrile, propionitrile, benzonitrile, dichloromethane, 1,2-dichloroethane, toluene, chloro-benzene, and the like. Sufficient organic solvent is employed to facilitate stirring of the reaction mixture and, thereby, to achieve homogeneity and promote good contact between the reagents.

The amount of 3-picoline or 3,5-lutidine employed in the reaction can range from stoichiometric with respect to the amount of aromatic sulfonyl chloride to a 6-fold or even greater excess. In fact, excess 3-picoline or 3,5-lutidine can effectively be used as the solvent; however, the addition of other solvents and acidification is typically required to conveniently recover the product.

The N-([1,2,4]triazolopyrimidin-2-yl)aryl sulfonamides of formula I can be recovered from the process medium by standard procedures, including by addition with an acidic aqueous phase and subsequent filtration of the product solids or solvent extraction; or by addition with a suitable organic solvent and filtration of the product solids; or by direct filtration of reaction solids and subsequent treatment of the solids to remove unwanted components. The products obtained on recovery can generally be purified by standard procedures, such as recrystallization.

The aromatic sulfonyl chloride compounds and the N-([1,2,4]-triazolopyrimidin-2-yl)amine compounds are known in the art or can be prepared by routine adaptation of the methods disclosed in the art.

The following examples are provided to illustrate the invention. They should not be construed as limiting the claims.

EXAMPLES

Unless stated otherwise, the following reactions were run under anhydrous conditions using dry solvents and nitrogen blanket and the 3-picoline and 3,5-lutidine bases were dried with molecular sieves before using. 3,5-Lutidine was used both as a high purity commercial form (99%) and also as a technical grade (90-95%) wherein the balance was primarily comprised of various alkylpyridines such as other lutidine isomers. For practical purposes, the technical material was used "as if" it were 100%. All assays reported are by HPLC, and are weight % based on comparison with pure standards unless stated otherwise. Starting material amounts are reported as grams of active unless noted otherwise.

Example 1

Preparation of 2-(2,2-Difluoroethoxy)-N-(5,8-dimethoxy-[1,2,4]triazolo[1,5-c]pyrimidin-2-yl)-6-(trifluoromethyl)benzenesulfonamide 2-Amino-5,8-dimethoxy[1,2,4]triazolo[1,5-c]pyrimidine (5.6 g, 0.029 mol) was slurried in dichloromethane (100 mL) and methyl sulfide (1.9 g, 0.031 mol) was added. The mixture was cooled to –25° C., and a solution of N-chlorosuccinimide (4.2 g, 0.031 mol) in acetonitrile (40 mL) was added to the reaction slurry over one hour, keeping the internal temperature at –22 to –28° C. When the addition was complete, the reaction was allowed to warm to room temperature over several hours. The new slurry was filtered and the solids washed with acetonitrile (2×40 mL). The solids were dried in a vacuum oven to provide 7.7 g of N-(5,8-dimethoxy[1,2,4]triazolo[1,5-c]pyrimidin-2-yl)-S,S-dimethylsulfilimine hydrochloride as a light tan solid, m.p. 170-174° C. The material was 95 area % pure by HPLC, with the remainder being the amine starting material.

The sulfilimine salt obtained above (0.3 g, 0.001 mol), 2-amino-5,8-dimethoxy[1,2,4]triazolo[1,5-c]pyrimidine (3.5 g, 0.018 mol) and 2-(2,2-difluoroethoxy)-6-(trifluoromethyl)benzenesulfonyl chloride (5.8 g, 0.018 mol) were combined in 3-picoline (11 g, 0.12 mol) and acetonitrile (50 mL). The slurry was stirred and heated at 48° C. for 20 hours. The mixture was then cooled to 30° C. and poured into 15% sulfuric acid (100 mL). The resulting slurry was stirred for one hour, then filtered, and the solids washed with water. After drying under vacuum at 55° C., 7.8 g product was obtained as a white solid assaying at 97 wt % (87% yield).

Example 2

Preparation of 2-(2,2-Difluoroethoxy)-N-(5,8-dimethoxy[1,2,4]-triazolo[1,5-c]pyrimidin-2-yl)-6-(trifluoromethyl)benzenesulfonamide A solution of methyl sulfide (0.34 g, 0.0055 mol) in acetonitrile (40 mL) was cooled to −25° C. To the cold solution was added a cold, freshly prepared 17 wt % solution of chlorine in acetonitrile (2.4 g, 0.0057 mol) over several minutes. While still cold, 1.1 g of 2-amino-5,8-dimethoxy[1,2,4]triazolo[1,5-c]pyrimidine (1.1 g, 0.0056 mol) and 3-picoline (0.95 g, 0.010 mol) were added. The mixture was allowed to warm to 8° C. 3-Picoline (48 g, 0.52 mol), 2-amino-5,8-dimethoxy[1,2,4]triazolo[1,5-c]pyrimidine (18.4 g, 0.094 mol), and 2-(2,2-difluoroethoxy)-6-(trifluoromethyl)benzenesulfonyl chloride (32.5 g, 0.10 mol) were added in order to the reactor. The mixture was stirred and heated at ~40° C. for 24 hours, then at room temperature for 48 hours. The reaction slurry was converted into a solution by the addition of acetonitrile (600 mL) and water (100 mL). The solution was assayed for product by HPLC and determined to contain 42 g (86% yield, in situ, from sulfonyl chloride).

Example 3

Preparation of N-(5,8-dimethoxy[1,2,4]triazolo[1,5-c]pyrimidin-2-yl)-2-methoxy-4-(trifluoromethyl)pyridine-3-sulfonamide 2-Amino-5,8-dimethoxy[1,2,4]triazolo[1,5-c]pyrimidine (98 g, 0.50 mol) and 147 g of 2-methoxy-4-(trifluoromethyl)pyridine-3-sulfonyl chloride (147 g, 0.53 mol, 1.06 eq) were combined in 3,5-lutidine (370 mL). After 10 minutes, 1.4 g of dimethyl sulfoxide (DMSO, 1.4 g, 0.018 mol) was added and a resulting exotherm raised the reaction temperature to 52° C. over 30-45 minutes, after which the mixture slowly returned to room temperature. After four hours, the reaction slurry was filtered and the cake washed with toluene (200 mL). The solids were triturated with a mixture of acetonitrile (250 mL) and 2 N HCl (400 mL). After stirring at room temperature for 45 minutes, the solids were filtered, washed with water (100 mL), and dried under vacuum to afford 197 g of product as a solid assaying at 97.6 wt % (88% yield from the amine; 83% yield from the sulfonyl chloride).

Example 4

Preparation of N-(5,7-dimethoxy[1,2,4]triazolo[1,5-a]pyrimidin-2-yl)-2-methoxy-4-(trifluoromethyl)pyridine-3-sulfonamide 2-Amino-5,7-dimethoxy[1,2,4]triazolo[1,5-a]pyrimidine (9.8 g, 0.050 mol) and N-(5,7-dimethoxy[1,2,4]triazolo[1,5-a]pyrimidin-2-yl)-S,S-dimethyl-sulfilimine hydrochloride salt (1.5 g, 0.005 mol) solids were combined with 2-methoxy-4-(trifluoromethyl)-pyridine-3-sulfonyl chloride (14 g, 0.051 mol) in acetonitrile (40 mL). 3,5-Lutidine (31 g, 93% technical) was added, and the mixture was stirred at room temperature for 22 hours. The mixture was warmed to 42° C. and treated with 3 N HCl (65 mL), after which the mixture was allowed to cool to room temperature over 1.5 hours. The solids were collected by filtration, washed with a 2:1 v/v solution of water:acetonitrile (20 mL), and dried under vacuum at 60° C. to afford 18 g of product assaying at 94 wt % (78% yield).

Example 5

Preparation of N-(5,7-dimethoxy[1,2,4]triazolo[1,5-a]pyrimidin-2-yl)-2-methoxy-4-(trifluoromethyl)pyridine-3-sulfonamide 2-Amino-5,7-dimethoxy[1,2,4]triazolo[1,5-a]pyrimidine (59 g, 0.30 mol) was combined with 2-methoxy-4-(trifluoromethyl)pyridine-3-sulfonyl chloride (86 g, 0.31 mol, 1.03 eq) in acetonitrile (210 mL) and 3,5-lutidine (120 g, 93% technical). DMSO (1.3 g, 0.017 mol) was added, and the mixture was stirred at room temperature for 12 hours. The mixture was then treated with 4 N HCl (310 mL), after which the mixture was stirred for another 2 hours at 25° C., then cooled to 10° C. The solids were collected by filtration, washed with a 2:1 v/v solution of water:acetonitrile (160 mL), washed with 95% ethanol (2×80 mL), and dried under vacuum at 100° C. to afford 112 g of product assaying at 98 wt % (84% yield from amine, 82% yield from sulfonyl chloride).

Example 6

Preparation of N-(5,8-Dimethoxy[1,2,4]triazolo[1,5-c]pyrimidin-2-yl)-2-methoxy-4-(trifluoromethyl)pyridine-3-sulfonamide 2-Amino-5,8-dimethoxy[1,2,4]triazolo[1,5-c]pyrimidine (19.5 g, 0.10 mol) and 2-methoxy-4-(trifluoromethyl)pyridine-3-sulfonyl chloride (27.5 g, 0.10 mol) were combined in acetonitrile (35 mL). To this was added 3,5-lutidine (32 g, 0.30 mol), followed by DMSO (0.23 g, 0.0030 mol). A slight exotherm was noted (to about 30° C.) in the initial hours as the reaction slurry was stirred at ambient conditions for 17 hours. The mixture was then warmed to 40° C. and treated with 2 N HCl (140 mL). The new slurry was stirred while being allowed to cool to room temperature over one hour. The solids were isolated by filtration, washed with water, and dried under vacuum to afford 38 g of product as a solid assaying at 97 wt % (85% yield).

Example 7

Preparation of 2-(2,2-Difluoroethoxy)-N-(5,8-dimethoxy-[1,2,4]triazolo[1,5-c]pyrimidin-2-yl)-6-(trifluoromethyl)benzenesulfonamide 2-Amino-5,8-dimethoxy[1,2,4]triazolo[1,5-c]pyrimidine (19.5 g, 0.10 mol) and 2-(2,2-difluoro-ethoxy)-6-(trifluoromethyl)benzenesulfonyl chloride (32.5 g, 0.10 mol) were combined in acetonitrile (45 mL) and 3,5-lutidine (17 g, 93% technical, ~0.16 mol) at room temperature. After 10 minutes, DMSO (0.20 g, 0.0026 mol) was added and the reaction slurry was stirred at room temperature for 24 hours. The mixture was then warmed to 48° C. and acidified by the addition of 2 N HCl (100 mL) over 30 minutes, during which the temperature was allowed to fall to ~38° C. The warm mixture was stirred for one hour, then cooled to 10° C. The precipitated solids were filtered, washed with water (30 mL), washed with methanol (75 mL), and dried under vacuum to afford 44 g of product as a light tan solid assaying at 98 wt % (89% yield).

Example 8

Preparation of 2-(2,2-Difluoroethoxy)-N-(5,8-dimethoxy-[1,2,4]triazo[1,5-c]pyrimidin-2-yl)-6-(trifluoromethyl)benzenesulfonamide 2-Amino-5,8-dimethoxy[1,2,4]triazolo[1,5-c]pyrimidine (39 g, 0.20 mol) and 2-(2,2-difluoroethoxy)-6-(trifluoromethyl)benzenesulfonyl chloride (65 g, 0.20 mol) were combined in acetonitrile (100 mL) and 3-picoline (95 g, 1.0 mol) at room temperature. After 30 minutes, DMSO (0.60 g, 0.0077 mol) was added and the reaction slurry was heated at ~44° C. for 4 hours, at which time an additional 38 g of 3-picoline was added. The reaction was heated for another 16 hours at ~44° C. The mixture was then warmed to 50° C. and acidified by the addition of 3 N HCl (430 mL) over 30 minutes, during which the temperature fell to ~37° C. The new slurry was allowed to cool to room temperature over 30 minutes. The precipitated solids were filtered, washed with water (150 mL), washed with ethanol (200 mL), and dried under vacuum to afford 81 g of product as a light tan solid assaying at 97 wt % (81% yield).

Example 9

Preparation of 2-(2,2-Difluoroethoxy)-N-(5,8-dimethoxy-[1,2,4]triazolo[1,5-c]pyrimidin-2-yl)-6-(trifluoromethyl)benzenesulfonamide 2-Amino-5,8-dimethoxy[1,2,4]triazolo[1,5-c]pyrimidine (7.8 g, 0.040 mol) and 2-(2,2-difluoroethoxy)-6-(trifluoromethyl)benzenesulfonyl chloride (13 g, 0.040 mol) were combined in 3,5-lutidine (31 g, 0.29 mol, 7.2 eq). The slurry was treated with methyl sulfoxide (0.040 g, 0.0005 mol, 0.012 eq) and stirred at ambient conditions for 8.5 hours. The reaction slurry was filtered, and the wet cake solids were slurried in a mixture of 15% sulfuric acid (80 mL) and acetonitrile (20 mL). The mixture was stirred for 25 minutes, then filtered, and the solids washed with water. After drying under vacuum at 55° C., 18 g of product was obtained as a white solid assaying at 97.4 wt % (91% yield).

Example 10

Preparation of 2-(2,2-Difluoroethoxy)-N-(5,8-dimethoxy-[1,2,4]triazolo[1,5-c]pyrimidin-2-yl)-6-(trifluoromethyl)benzenesulfonamide 2-Amino-5,8-dimethoxy[1,2,4]triazolo[1,5-c]pyrimidine (7.8 g, 0.040 mol) and 2-(2,2-difluoroethoxy)-6-(trifluoromethyl)benzenesulfonyl chloride (13 g, 0.040 mol) were combined in 3,5-lutidine (31 g, 0.29 mol). The slurry was treated with DMSO (0.040 g, 0.012 eq) and stirred at ambient conditions for 8.5 hours, with a slight rise in temperature noted in the first hours resulting from a reaction exotherm. The reaction slurry was filtered, and the wet cake solids were transferred to a separate vessel and slurried in a mixture of 15% sulfuric acid (80 mL) and acetonitrile (20 mL). The mixture was stirred for 25 minutes, then filtered and the solids washed with water. After drying under vacuum at 55° C., 18 g of product was obtained as a white solid assaying at 97 wt % (90% yield).

What is claimed is:

1. An improved process for the preparation of an N-([1,2,4]triazolopyrimidin-2-yl)aryl sulfonamide of formula I:

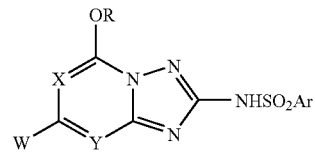

wherein
 X represents CH or N;
 Y represents CZ or N with the proviso that only one of X or Y is N;
 W represents H or OR with the proviso that when Y represents CZ, then W represents H;
 Z represents OR;
 R represent $CH_3$ or $CH_2CH_3$;
 Ar represents

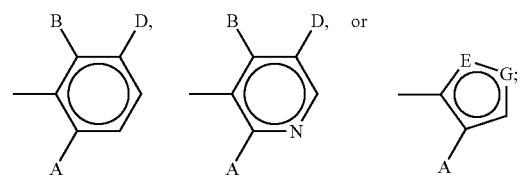

wherein
 A and B independently represent H, halo, $CF_3$, R or $OR^1$;
 D represents H, halo or R;
 E and G represent S or CB with the proviso that one of E or G is S; and
 $R^1$ represents $C_1$-$C_4$ alkyl, $C_3$-$C_4$ alkenyl, or $C_3$-$C_4$ alkynyl each optionally possessing up to two chloro, bromo or $C_1$-$C_4$ alkyl substituents or up to the maximum possible number of fluoro substituents
which comprises combining a sulfonyl chloride compound of the formula:

wherein
 Ar is defined as above
with an amine compound of the formula:

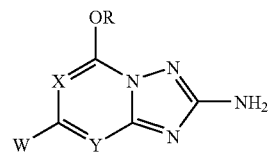

wherein
R, X, Y and W are defined as above
in the presence of an aromatic tertiary amine base and a catalytic amount of an N-aryl-sulfilimine compound of the formula:

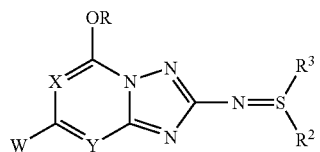

wherein
R, X, Y and W are defined as above;
$R^2$ represents $CH_3$, or $CH_2CH_3$; and
$R^3$ represents $R^2$ or $R^2$ and $R^3$ together represent tetramethylene or their salts, wherein the improvement comprises using 3-picoline or 3,5-lutidine as the aromatic tertiary amine base.

2. The process of claim 1 which $R^2$ and $R^3$ each represent $CH_3$.

3. The process of claim 1 in which the N-arylsulfilimine compound is in the form of the HCl or HBr salt.

* * * * *